(12) United States Patent
Zhan et al.

(10) Patent No.: US 11,237,281 B2
(45) Date of Patent: Feb. 1, 2022

(54) FLAT-PANEL DETECTOR COMPRISING LIGHT-TRANSMISSION LAYER BETWEEN RAY-CONVERSION LAYER AND PHOTOELECTRIC CONVERSION LAYER AND METHOD OF MANUFACTURING FLAT-PANEL DETECTOR

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Xiangmi Zhan, Beijing (CN); Xuecheng Hou, Beijing (CN); Cheng Li, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 16/526,852

(22) Filed: Jul. 30, 2019

(65) Prior Publication Data
US 2020/0158892 A1   May 21, 2020

(30) Foreign Application Priority Data
Nov. 20, 2018   (CN) .......................... 201811384620.4

(51) Int. Cl.
*A61B 6/00* (2006.01)
*G01T 1/20* (2006.01)
(Continued)

(52) U.S. Cl.
CPC ............ *G01T 1/20185* (2020.05); *A61B 6/42* (2013.01); *A61B 6/4208* (2013.01);
(Continued)

(58) Field of Classification Search
CPC ....... A61B 6/42; A61B 6/4208; A61B 6/4233; G01T 1/2006; G01T 1/2018;
(Continued)

(56) References Cited

U.S. PATENT DOCUMENTS 5,059,800 A * 10/1991 Cueman .................. G01T 1/202
 250/367
5,150,394 A * 9/1992 Karellas ............... A61B 6/4241
 250/252.1

(Continued)

FOREIGN PATENT DOCUMENTS

CN   1257415 A   6/2000
CN   101509977 A   8/2009

(Continued)

OTHER PUBLICATIONS

First Chinese Office Action dated May 8, 2020, for corresponding Chinese Application No. 201811384620.4.

*Primary Examiner* — Allen C. Ho
(74) *Attorney, Agent, or Firm* — Kinney & Lange, P.A.

(57) ABSTRACT

A flat-panel detector includes: a ray-conversion layer configured to convert rays into a light having a first wavelength; and a plurality of imaging units. At least one of the plurality of imaging units includes: a photo sensor configured for receiving the light and converting the light to an electrical signal; and a light guider located a side of the photo sensor adjacent to the ray-conversion layer, the light guider having a light entry surface adjacent to the ray-conversion layer and a light exit surface adjacent to the photo sensor, the light entry surface being configured to receive the light from the ray-conversion layer and having an area greater than an area of the light exit surface, and an orthogonal projection of the light exit surface in a direction perpendicular to the ray-conversion layer at least partially overlapping that of the photo sensor.

12 Claims, 3 Drawing Sheets

(51) Int. Cl.
*G01T 1/202* (2006.01)
*G21K 4/00* (2006.01)

(52) U.S. Cl.
CPC .......... *A61B 6/4233* (2013.01); *G01T 1/2002* (2013.01); *G01T 1/2006* (2013.01); *G01T 1/2018* (2013.01); *G01T 1/2023* (2013.01); *G01T 1/20183* (2020.05); *G01T 1/20184* (2020.05); *G21K 2004/02* (2013.01)

(58) Field of Classification Search
CPC ... G01T 1/20183; G01T 1/20185; G01T 1/20; G01T 1/2002
USPC .................................. 378/98.8; 250/370.09
See application file for complete search history.

(56) References Cited

U.S. PATENT DOCUMENTS

| | | | | |
|---|---|---|---|---|
| 5,391,879 A * | 2/1995 | Tran | ...................... | G01T 1/2018 250/367 |
| 5,550,380 A * | 8/1996 | Sugawara | .............. | A61B 6/145 250/370.11 |
| 5,563,414 A * | 10/1996 | Sklebitz | .............. | H01L 25/0655 250/367 |
| 5,572,034 A * | 11/1996 | Karellas | ................ | G01T 1/2018 250/367 |
| 5,594,253 A * | 1/1997 | Bueno | ..................... | G01T 1/201 250/367 |
| 5,636,299 A * | 6/1997 | Bueno | ..................... | G01T 1/201 250/367 |
| 5,682,411 A * | 10/1997 | Rushbrooke | ......... | H04N 5/2254 348/E3.02 |
| 5,715,292 A * | 2/1998 | Sayag | .................. | A61B 6/4233 250/368 |
| 5,793,838 A * | 8/1998 | Kovacs | .................... | A61B 6/14 378/39 |
| 5,864,146 A * | 1/1999 | Karellas | ................... | A61B 6/06 250/581 |
| 6,005,911 A * | 12/1999 | Cheung | ................ | A61B 6/4233 378/37 |
| 6,031,892 A * | 2/2000 | Karellas | ................... | A61B 6/06 250/370.09 |
| 6,042,267 A * | 3/2000 | Muraki | ................. | G01T 1/2018 348/E5.086 |
| 6,087,665 A * | 7/2000 | Hoffman | ................ | A61B 6/032 250/367 |
| 6,285,739 B1 * | 9/2001 | Rudin | .................. | A61B 6/4233 378/62 |
| 6,448,544 B1 * | 9/2002 | Stanton | ................. | G01T 1/2928 250/208.1 |
| 6,472,665 B1 * | 10/2002 | Ishisaka | ................ | G01T 1/2018 250/368 |
| 6,479,827 B1 * | 11/2002 | Hamamoto | .......... | H01L 27/146 250/370.11 |
| 6,528,796 B1 * | 3/2003 | Kaifu | .................... | G01T 1/2018 250/370.09 |
| 6,559,452 B1 * | 5/2003 | Tashiro | ................. | G01T 1/2928 250/366 |
| 6,635,877 B2 * | 10/2003 | Kusuyama | ........... | G01T 1/2018 250/367 |
| 6,781,131 B2 * | 8/2004 | Kusuyama | ........... | G01T 1/2002 250/368 |
| 6,906,332 B2 * | 6/2005 | Tashiro | ................. | G01T 1/2928 250/208.1 |
| 7,010,091 B2 * | 3/2006 | Hayashida | ................ | G01T 1/17 250/370.09 |
| 7,071,980 B2 * | 7/2006 | Yuki | ..................... | H04N 3/1562 348/308 |
| 7,135,686 B1 * | 11/2006 | Grady | ................... | G01T 1/2018 250/370.11 |
| 7,692,156 B1 * | 4/2010 | Nagarkar | .............. | G01T 1/1644 250/370.11 |
| 8,519,338 B2 * | 8/2013 | Barrett | ................. | G01T 1/2018 250/361 R |
| 9,050,051 B2 * | 6/2015 | Nakatsugawa | ........ | G03B 42/04 |
| 10,517,545 B2 * | 12/2019 | Zhang | .................... | A61B 6/032 |
| 11,103,207 B1 * | 8/2021 | Singh | ...................... | H05G 1/20 |

FOREIGN PATENT DOCUMENTS

| | | |
|---|---|---|
| CN | 105304656 A | 2/2016 |
| CN | 107195647 A | 9/2017 |
| EP | 1000581 B1 | 2/2007 |
| JP | H1012851 A | 1/1998 |
| JP | 2012159483 A | 8/2012 |

* cited by examiner

FLAT-PANEL DETECTOR COMPRISING LIGHT-TRANSMISSION LAYER BETWEEN RAY-CONVERSION LAYER AND PHOTOELECTRIC CONVERSION LAYER AND METHOD OF MANUFACTURING FLAT-PANEL DETECTOR

CROSS-REFERENCE TO RELATED APPLICATION

This application claims the benefit of Chinese Patent Application No. 201811384620.4, entitled "Flat panel detector and method of manufacturing the same," filed with the State Intellectual Property Office of China on Nov. 20, 2018, the whole disclosure of which is incorporated herein by reference.

BACKGROUND

Technical Field

Embodiments of the present disclosure relate to the field of flat panel detectors, and particularly to a flat panel detector and a method of manufacturing the same.

Description of Related Art

Flat-panel detectors have a wide range of applications in medical imaging and industrial inspection. Since functions of light absorption, conversion and signal reading are necessarily achieved by means of thin film transistors and PIN photodiodes, while these types of detectors have a disadvantage of a low filling rate due to an inherent size of thin film transistors, a PIN photo sensor has a reduced light absorption area and thus a reduced detection sensitivity.

SUMMARY

Embodiments of the present disclosure provide a flat-panel detector and a method of manufacturing the same, which at least increase a filling rate, a light absorbing area and a detecting sensitivity of an amorphous silicon flat-panel detector.

Embodiments of the present disclosure provide a flat-panel detector, including:

a-ray conversion layer configured to convert a ray into a light having a first wavelength; and a plurality of imaging units, at least one of the imaging units comprising:

a photo sensor configured for receiving the light and converting the light to an electrical signal; and a light guider located a side of the photo sensor adjacent to the ray-conversion layer, the light guider having a light entry surface adjacent to the ray-conversion layer and a light exit surface adjacent to the photo sensor, the light entry surface being configured to receive the light from the ray-conversion layer and having an area greater than an area of the light exit surface, and an orthogonal projection of the light exit surface in a direction perpendicular to the ray-conversion layer at least partially overlapping that of the photo sensor.

In an embodiment, at least one of the imaging units further comprises: a read circuit electrically connected to the photo sensor and configured to read a signal provided by the photo sensor.

In an embodiment, the light guider comprises a fiber optic taper comprising a first end and a second end that are opposite to each other, the first end is the light entry portion, the second end is the light exit portion, and the fiber optic taper is disposed in one-to-one correspondence with the photo sensor so that the light having the first wavelength is transmitted, via the light exit surface of the second end of the fiber optic taper, to the photo sensor.

In an embodiment, a reflective layer is disposed on a tapered wall of the fiber optic taper.

In an embodiment, the photo sensor comprises a photodiode, and an orthogonal projection of the second end of the fiber optic taper in a direction perpendicular to the ray-conversion layer coincides with that of the photodiode.

In an embodiment, the read circuit comprises at least one of the group of an amorphous silicon thin film transistor, an oxide thin film transistor and an polysilicon thin film transistor.

In an embodiment, the flat-panel detector further includes a light-shielding layer disposed between the read circuit and the ray-conversion layer.

In an embodiment, the flat-panel detector further includes a passivation layer disposed on a side of the light-shielding layer facing away from the read circuit.

In an embodiment, the photodiode is connected to a drain electrode of the read circuit through a conductive element formed from a metal layer.

In an embodiment, the ray-conversion layer comprises an array of cesium iodide scintillation crystals or $Gd_2O_2S$:Tb particles.

In an embodiment, the light having the first wavelength ranged from 400 nm to 800 nm.

Embodiments of the present disclosure further provide a method of manufacturing the above mentioned flat-panel detector, the method including steps of:

forming sequentially a photoelectric conversion layer comprising the photo sensor, a light transmission layer comprising the light guider, and the ray-conversion layer.

In an embodiment, the fiber optic taper is provided with a reflective layer that is made of metal on a tapered wall thereof, and the reflective layer is formed by depositing a metal material on the tapered wall of each of the fiber optic tapers by a magnetron sputtering method or a electroplating method.

In an embodiment, the forming sequentially the photoelectric conversion layer, the light transmission layer, and the ray-conversion layer comprises:

forming an amorphous silicon thin film transistor on the substrate;

forming a first metal layer on the substrate on which the previous step is performed and bridging the first metal layer with a drain electrode of the amorphous silicon thin film transistor via a through hole as an extension of the drain electrode;

forming a photodiode as a photo sensor on the substrate on which the previous steps are completed;

coupling a light exit surface of the fiber optic taper right above the photodiode; and vapor depositing or bonding scintillators of a material onto the light entry surfaces of the fiber optic taper, and arranging them in array as the ray-conversion layer.

In an embodiment, the method further includes: after forming the photodiode, forming a second metal layer over the photodiode, and then, simultaneously forming a signal line and a light-shield layer covering the amorphous silicon thin film transistor by a single patterning process.

In an embodiment, the method further includes: after forming the light-shielding layer, coating a resin material or depositing a transparent passivation film layer to form a passivation layer.

DETAILED DESCRIPTION

The present disclosure will be further described in detail below in conjunction with the drawings and specific embodiments.

Figure 1:
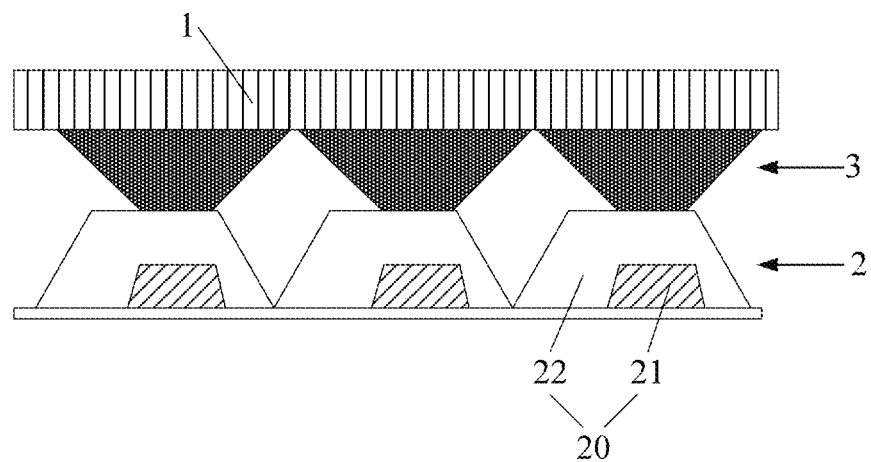
FIG. 1 is a schematic structural view of a flat-panel detector according to an embodiment of the present disclosure.
Figure 2:
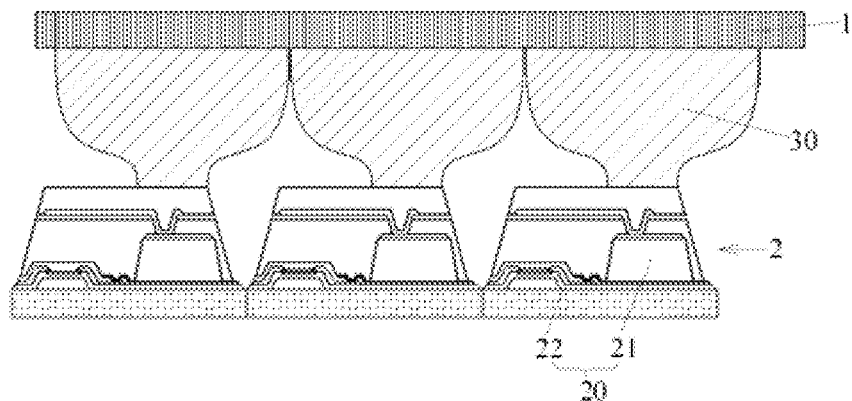
FIG. 2 is a schematic structural view of a flat-panel detector according to an embodiment of the present disclosure.

Embodiments of the present disclosure provide a flat-panel detector, as shown in FIG. 1, including a ray-conversion layer 1, a photoelectric conversion layer 2, and a light transmission layer 3. In the embodiment, the light transmission layer 3 is provided between the ray-conversion layer 1 and the photoelectric conversion layer 2. The ray-conversion layer 1 is provided to convert a ray into a light having a first wavelength. The first wavelength is greater than a wavelength of the ray. In the embodiment, the first wavelength may be in a range from 800 nm to 100000 nm (i.e., the light is an infrared wave light), or in a range from 400 nm to 800 nm (i.e., the light is visible light), or in a range from 100 nm to 400 nm (i.e., the light is ultraviolet light). In an embodiment, the first wavelength is ranged from 400 nm to 800 nm. The light transmission layer 3 is capable of transmitting the light having the first wavelength converted by the ray-conversion layer 1 to the photoelectric conversion layer 2.

In an embodiment, the light transmission layer 3 includes a light entry portion and a light exit portion, and the light transmission layer 3 is disposed such that an area of a light entry surface of the light entry portion is greater than an area of a light exit surface of the light exit portion, and the light entry portion is adjacent to the ray-conversion layer 1 such that the light having the first wavelength converted by the ray-conversion layer 1 enters the light transmission layer 3 through the light entry portion and is converged in the light transmission layer 3 and then is passed through the light exit portion to the photoelectric conversion layer 2. The photoelectric conversion layer 2 is configured to convert the light having the first wavelength received into an electrical signal for being read.

In an embodiment, the ray-conversion layer 1 may be an X-rays conversion layer; in an embodiment, the ray-conversion layer 1 may be a Gamma ray-conversion layer; in another embodiment, the ray-conversion layer 1 may be a conversion layer for converting another type of ray.

In an embodiment, the photoelectric conversion layer 2 may include a plurality of conversion units 20, each including a photo sensor 21 and a read circuit 22 connected to the photo sensor 21. The photo sensor 21 is provided for receiving the light having the first wavelength from the light exit portion of the light transmission layer 3 and converting the light having the first wavelength into the electrical signal. The read circuit 22 is provided for reading the electrical signal of the photo sensor 21.

The flat-panel detector according to the embodiment collects the light having the first wavelength converted by the ray-conversion layer 1 by using the light entry surface of the light transmission layer 3 having a greater area and after convergence, transmits it, by the light exit surface having a smaller area, to the photo sensor 21, which is equivalent to an improvement of a rate of absorption of the light having the first wavelength of the ray-conversion layer 1 by the photo sensor 21 and an improvement of a detection sensitivity. The flat-panel detector may be used in medical applications to reduce a ray radiation dose absorbed by a patient while protecting medical personnel.

In an embodiment, there is provided a flat-panel detector including: a ray-conversion layer 1 configured to convert a ray into a light having a first wavelength, the first wavelength being greater than a wavelength of the ray; and a plurality of imaging units 20. In the embodiment, each of the plurality of imaging units 20 includes: a photo sensor 21 configured for receiving the light and converting the light to an electrical signal; and a light guider 3 located a side of the photo sensor 21 adjacent to the ray-conversion layer 1, the light guider 3 having a light entry surface adjacent to the ray-conversion layer 1 and a light exit surface adjacent to the photo sensor 21. The light entry surface is configured to receive the light from the ray-conversion layer 1 and has an area greater than an area of the light exit surface, and an orthogonal projection of the light exit surface in a direction perpendicular to the ray-conversion layer 1 at least partially overlaps that of the photo sensor 21. In an embodiment, the flat-panel detector may include a base substrate and the ray-conversion layer 1 is located on the based substrate and the plurality of imaging units 20 are located between the base substrate and the ray-conversion layer 1. However, it is noted that a base substrate is not necessary for the present disclosure.

In an embodiment, each of the plurality of imaging units 20 further includes a read circuit 22 electrically connected to the photo sensor 21 and configured to read a signal provided by the photo sensor 21. The read circuit 22 comprises at least one of the group of an amorphous silicon thin film transistor, an oxide thin film transistor and an polysilicon thin film transistor. In an embodiment, the first wavelength may be ranged from 400 nm to 800 nm.

It is noted that in the above embodiments a term of imaging unit 20 is used and it in fact is a name of a combination of the photo sensor 21 and the light guider 3 or a combination of the photo sensor 21, the light guider 3 and the read circuit 22. Another different name may be used by those skilled in the art for the above combination and the different used name does not mean a new component being added. In another embodiment, components of the flat-panel detector according to the present disclosure are described by reference to layer(s).

Embodiments of the present disclosure provide a flat-panel detector, as shown in FIGS. 2-8, including a ray-conversion layer 1, a photoelectric conversion layer 2, and a light transmission layer 3, wherein the light transmission layer 3 is disposed between the ray-conversion layer 1 and the photoelectric conversion layer 2. The photoelectric conversion layer 2 may include a plurality of conversion units 20, each including a photo sensor 21 and a read circuit 22 connected to the photo sensor 21. The light transmission layer 3 includes a plurality of fiber optic tapers 30 arranged in one-to-one correspondence with the photo sensor 21 of the plurality of conversion units 20.

Figure 4:
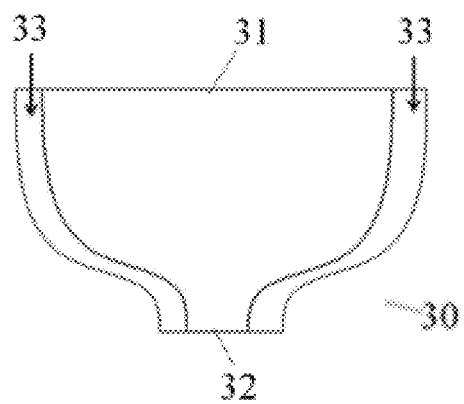
FIG. 4 is a schematic structural view of one fiber optic taper of an embodiment of the present disclosure.

In an embodiment, as shown in FIG. 4, the fiber optic taper 30 has a first end 31 and a second end 32 opposite to each other. The first end 31 is the light entry portion, and the second end 32 is the light exit portion. The area of the light entry surface of the first end 31 is greater than the area of the light exit surface of the second end 32. The fiber optic tapers 30 are arranged in one-to-one correspondence with the photo sensor 21 of the plurality of conversion units 20 so that the light having the first wavelength is transmitted from the light exit surfaces of the second end 32 of each of the fiber optic tapers 30 to one of the photo sensors 21. The light having the first wavelength entering the fiber optic taper 30 from the ray-conversion layer 1 can be converged and then transmitted by the fiber optic taper 30 to the photo sensor 21.

In an embodiment, the ray-conversion layer 1 converts entered rays into a light having the first wavelength, which is of about 550 nm, then the fiber optic tapers 30 converge the light having the first wavelength and transmits it, via the second end 32, to the photo sensor 21, and the photo sensor 21 receives the light having the first wavelength from the light exit portion of the light transmission layer 3 and converts it into an electrical signal. The read circuit 22 is used to read the electrical signal of the photo sensor 21. It should be understood that in another embodiment, the ray-conversion layer 1 can convert the entered rays into a light having other wavelengths, such as in a range from 400 nm to 800 nm, i.e., visible light.

In the embodiment, the fiber optic tapers 30 may be an image transmission device including a plurality of optical fibers with a diameter in a range from 5 μm to 6 μm. The optical fibers are regularly arranged in a certain shape, such as a circular shape, an elliptic shape, a rectangular shape, etc., which may be designed depending on actual conditions. Further, each fiber is formed in a tapered shape by uniformly stretching at one end. It should be understood that the fiber optic taper 30 may be in a regular pyramidal or conical shape as a whole, however, the fiber optic taper 30 may be partially in a pyramidal or conical shape, but as a whole is not in a strictly pyramidal or conical shape, provided it could converge light. In a general ray detection, the presence of the light having the first wavelength in the detector indicates that a ray is detected, achieving a simple ray detection function.

In an embodiment, the fiber optic taper 30 has a function of enlarging or reducing an image, which requires that the fiber optic taper 30 should have not only a function of converging light, but also a regular shape so that the convergence of light is uniform. Specifically, the fiber optic taper 30 may be an image transmission device that can provide a distortion-free image transmission with an image enlarged or reduced, and a magnification or a reduction ratio is equal to a ratio between diameters of two end faces of the fiber optic taper. The fiber optic taper 30 used herein may be an image transmission device that transmits an image with reducing the image without distortion. Similar to other fiber optic components, each of the fiber optic tapers 30 has optical insulation property and can independently transmit light without being affected by adjacent optical fibers. When an image is inputted to ends of the fiber optic tapers 30, the image is decomposed by tens of millions of fibers included by the fiber optic tapers 30 into image elements each corresponding to one fiber. The fibers that are regularly arranged will transmit the image element information carried by them to the other ends of the fiber optic tapers. The image elements are enlarged or reduced with changing of the diameter of each of the optical fibers (each having a circular light entry surface and a circular light exit surface) or a side length of each of the optical fibers (each having a rectangular light entry surface and a rectangular light exit surface) during transmission of the image, and are combined into an image on the light exit surfaces in their original arrangement. The specific shape of the fiber optic taper 30 is not limited herein. For example, the fiber optic taper 30 may have a circular or a rectangular shape.

Figure 3:
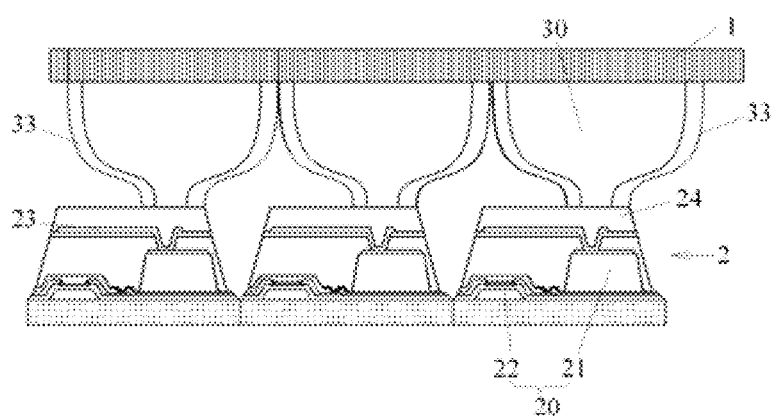
FIG. 3 is another schematic structural view of a flat-panel detector according to an embodiment of the present disclosure.

In an embodiment, as shown in FIGS. 3 and 4, a reflective layer 33 may be disposed on a tapered wall of each of the fiber optic tapers 30.

In the embodiment, the reflective layer 33 is configured to prevent lateral diffusion of a light having the first wavelength between adjacent ones of the fiber optic tapers 30, and thus to prevent light crosstalk between adjacent ones of the fiber optic tapers 30.

In an embodiment, the reflective layer 33 is made of a metallic material.

For example, the reflective layer 33 may be made of an aluminum (Al) material, as Al has a high reflectance and is easy to be coated.

Figure 5:
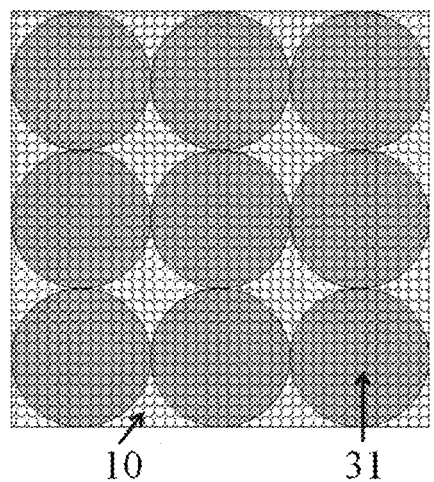
FIG. 5 is a top view of a fiber optic taper of an embodiment of the present disclosure.
Figure 6:
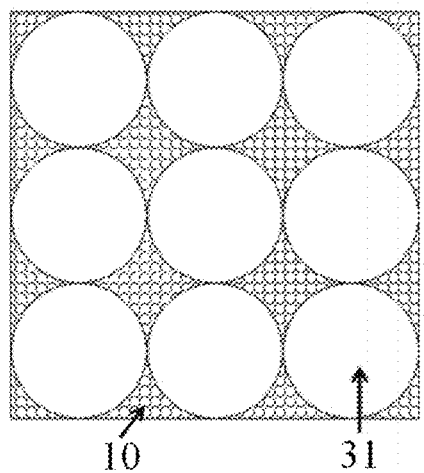
FIG. 6 is a bottom view of a fiber optic taper of an embodiment of the present disclosure.

In an embodiment, as shown in FIGS. 5 and 6, the ray-conversion layer 1 is composed of an array of cesium iodide scintillation crystals 10 or GOS ($Gd_2O_2S:Tb$) particles.

Specifically, the array of cesium iodide scintillation crystals 10 include a plurality of cesium iodide scintillation crystals that are in an acicular shape and independent of each other. Herein, an acicular shape may be specifically a cylindrical shape or a shape close to a cylinder. Generally, a thickness of the ray-conversion layer 1 formed by the array of cesium iodide scintillation crystals 10 may be in a range from 100 μm to 1000 μm, however, the specific thickness of the ray-conversion layer 1 is not limited thereto.

Figure 7:
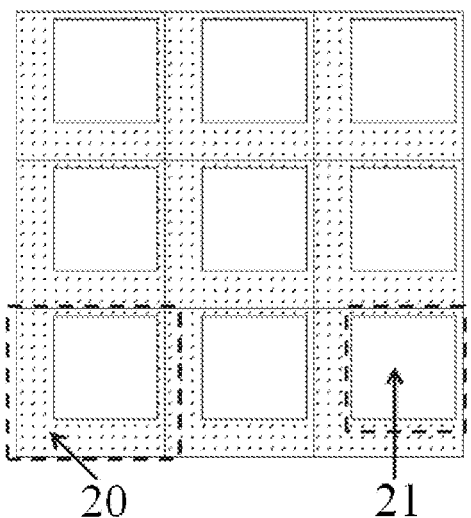
FIG. 7 is a schematic top view of a conversion unit of an embodiment of the present disclosure.
Figure 8:
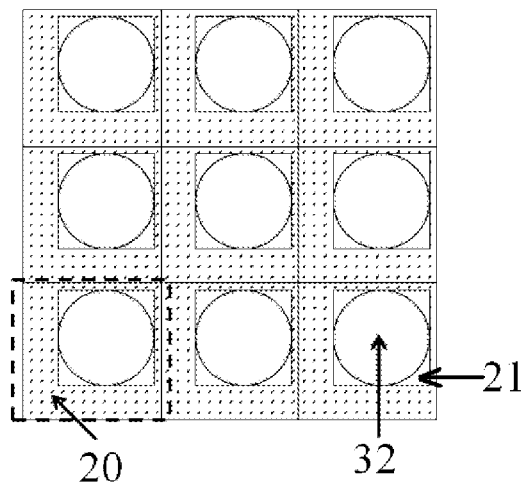
FIG. 8 is a bottom view of a conversion unit of an embodiment of the present disclosure.

In an embodiment, the photo sensor 21 includes a photodiode. As shown in FIGS. 7 and 8, an orthogonal projection of the second end 32 of the fiber optic taper 30 in a direction perpendicular to the ray-conversion layer 1 is coincident with that of the photodiode in the direction perpendicular to the ray-conversion layer 1.

In the embodiment, the photodiode converts the light having the first wavelength into a positive electric charge signal and a negative electric charge signal under the action of the light having the first wavelength irradiation.

In an embodiment, the read circuit 22 includes an amorphous silicon thin film transistor. In an embodiment, the read circuit 22 performs control by the amorphous silicon thin film transistor, and reads the electrical signal converted by the photodiode and sends it to a signal storage unit (not shown), so as to obtain an image information upon a further amplification and A/D conversion.

In an embodiment, the orthogonal projection of the amorphous silicon thin film transistor in the direction perpendicular to the ray-conversion layer 1 does not overlap that of the photodiode.

In an embodiment, during manufacturing the flat-panel detector, the amorphous silicon thin film transistor is formed firstly, and then the photodiode is formed. If the orthogonal projection of the crystalline silicon thin film transistor in the direction perpendicular to the ray-conversion layer 1 overlaps with that of the photodiode, that is, the photodiode is formed on the amorphous silicon thin film transistor, the subsequent formation of the photodiode may adversely affect the amorphous silicon thin film transistor. According to an embodiment of the present disclosure, the amorphous silicon thin film transistor and the photodiode are configured such that their orthogonal projections in the direction perpendicular to the ray-conversion layer 1 do not overlap and damage to the amorphous silicon thin film transistor can be avoided.

In an embodiment, the photodiode is connected to a drain electrode of the amorphous silicon thin film transistor by a wire formed by a metal layer.

In this configuration, it is equivalent to extend the drain electrode of the amorphous silicon thin film transistor, thereby facilitating connection with the photodiode, and a surface of the extending metal layer is smooth with less etching damage, which is favorable to obtaining photodiode with a high quality and further avoiding peel-off phenomenon of the photodiode.

In an embodiment, a light-shielding layer 23 is disposed between the amorphous silicon thin film transistor and the ray-conversion layer 1. As shown in FIG. 3, a light-shielding layer 23 is disposed over and covers the amorphous silicon thin film transistor to obtain a further protection of the amorphous silicon thin film transistor from light radiation.

In an embodiment, the photoelectric conversion layer 2 may further include a signal line connected to the photodiode, the signal line being disposed between the photodiode and the light transmission layer 3, and being usually made of metal.

In the embodiment, the light-shielding layer 23 is also made of metal, and the light-shielding layer 23 may be in the same layer as the signal line, that is, the signal line may be formed with the light-shielding layer 23 by a single patterning process.

In an embodiment, a passivation layer 24 is provided on a side of the light-shielding layer 23 that faces away from the amorphous silicon thin film transistor.

According to the present embodiment, the passivation layer 24 is provided between the light transmission layer 3 and the photoelectric conversion layer 2 including the amorphous silicon thin film transistor and the photodiode to obtain a planarization and a protection of the photoelectric conversion layer 2.

In the drawings corresponding to the present embodiments, sizes, thicknesses, and the like of the structural layers shown in the drawings are shown for illustration. In the process implementation, projected areas of the structural layers on the substrate may be the same or different.

Embodiments of the present disclosure provide a method for manufacturing the above flat-panel detector, as shown in FIG. 3, including the following steps.

In step S01, an amorphous silicon thin film transistor is formed on a substrate. Specifically, a top gate type or a bottom gate type amorphous silicon thin film transistor can be formed on the substrate to fabricate a read circuit 22.

In step S02, a first metal layer is deposited on the substrate on which the above step is completed, and the first metal layer is bridged with a drain electrode of the above thin film transistor via a through hole as an extension of the drain electrode. This configuration may ensure a film layer above it to have a good deposition quality and prevent the film layer from peeling off.

In step S03, a photodiode is formed as a photo sensor 21 on the substrate on which the above steps are completed, a passivation layer is deposited by a single process or a resin is coated, and a signal line which is connected to the photodiode via a through hole is prepared. In an embodiment, the amorphous silicon thin film transistor and the photodiode may be arranged such that their orthogonal projections in a direction perpendicular to the ray-conversion layer 1 have no overlapping. It should be noted that, in the embodiment, a second metal layer may be formed over the photodiode, and may be formed simultaneously by a single patterning process into the signal line and the light-shielding layer 23 of the amorphous silicon thin film transistor.

In step S04, a passivation layer 24 is formed by coating a layer of resin material or depositing another transparent passivation film layer.

In step S05, a second end 32 of each of the fiber optic tapers 30 is coupled to right above the photodiode, wherein the second end 32 of each of the fiber optic tapers matches a size of the photodiode, i.e., the faces of them opposing to each other have the same area.

As an example of the embodiment, the step further includes a step of forming a reflective layer 33 that is made of metal on the tapered wall of each of the fiber optic tapers 30. Specifically, the reflective layer 33 that is made of metal may be formed by depositing a metal material on the tapered wall of each of the fiber optic tapers 30 by a magnetron sputtering method or an electroplating method.

In step S06, scintillators of a material such as CsI or GOS are vapor-deposited or bonded on the first ends 31 of the fiber optic tapers 30, respectively, and arrayed in order to form an array as the ray-conversion layer 1.

It is understood that the above embodiments are merely exemplary embodiments employed to explain the principles of the present disclosure, but the present disclosure is not limited thereto. Various modifications and improvements can be made by those skilled in the art without departing from the spirit and scope of the disclosure, and such modifications and improvements are also considered as falling within the scope of the present disclosure.

What is claimed is:

1. A flat-panel detector comprising:
   a ray-conversion layer configured to convert a ray into a light having a first wavelength; and
   a plurality of imaging units, at least one imaging unit of the plurality of imaging units comprising:
      a photo sensor configured for receiving the light and converting the light to an electrical signal;
      a light guider located at a first side of the photo sensor adjacent to the ray-conversion layer, the light guider having a light entry surface adjacent to the ray-conversion layer and a light exit surface adjacent to the photo sensor, the light entry surface being configured to receive the light from the ray-conversion layer and having an area greater than an area of the light exit surface, and an orthogonal projection of the light exit surface in a direction perpendicular to the ray-conversion layer at least partially overlapping that of the photo sensor; and
      a read circuit electrically connected to the photo sensor and configured to read the electrical signal provided by the photo sensor; and
      wherein the light guider comprises:
         a fiber optic taper comprising a first end and a second end that are opposite to each other, the first end is a light entry portion, the second end is a light exit portion, and the fiber optic taper is disposed in a one-to-one correspondence with the photo sensor so that the light having the first wavelength is transmitted, via the light exit portion of the second end of the fiber optic taper, to the photo sensor; and a reflective layer disposed on a tapered wall of the fiber optic taper.

2. The flat-panel detector as claimed in claim 1, wherein the photo sensor comprises: a photodiode, wherein an orthogonal projection of the second end of the fiber optic taper in a direction perpendicular to the ray-conversion layer coincides with that of the photodiode.

3. The flat-panel detector as claimed in claim 1, wherein the read circuit comprises at least one transistor selected from the group consisting of an amorphous-silicon thin-film transistor, an oxide thin-film transistor, and a polysilicon thin: film transistor.

4. The flat-panel detector as claimed in claim 3, further comprising: a light-shielding layer disposed between the read circuit and the ray-conversion layer.

5. The flat-panel detector as claimed in claim 4, further comprising: a passivation layer disposed on a side of the light-shielding layer facing away from the read circuit.

6. The flat-panel detector as claimed in claim 4, further comprising:

a metal layer comprising a conductive element, wherein the read circuit comprises a drain electrode wherein the photo sensor comprises a photodiode connected to the drain electrode through the conductive element.

7. The flat-panel detector as claimed in claim 1, wherein the ray-conversion layer comprises an array of cesium iodide scintillation crystals or $Gd_2O_2S$:Tb particles.

8. The flat-panel detector as claimed in claim 1, wherein the first wavelength ranges from 400 nm to 800 nm.

9. A method of manufacturing a flat-panel detector comprising steps of:

forming sequentially a photoelectric conversion layer comprising a photo sensor, a light-transmission layer comprising a light guider, and a ray-conversion layer, and providing a fiber optic taper with a reflective layer comprising a metal material on a tapered wall of the fiber optic taper, and wherein providing the fiber optic taper with the reflective layer comprising the metal material comprises depositing the metal material on the tapered wall of the fiber optic taper by a magnetron sputtering method or an electroplating method.

10. The method as claimed in claim 9, wherein forming sequentially the photoelectric conversion layer, the light-transmission layer, and the ray-conversion layer comprises:

forming an amorphous-silicon thin-film transistor on a substrate;

forming a first metal layer on the substrate on which the previous forming step is performed and bridging the first metal layer with a drain electrode of the amorphous-silicon thin-film transistor via a through hole as an extension of the drain electrode;

forming a photodiode as a photo sensor on the substrate on which the previous forming steps are completed;

coupling a light exit surface of a fiber optic taper right above the photodiode;

vapor depositing or bonding scintillators of a material onto light entry surfaces of the fiber optic taper, and arranging the scintillators of the material in an array as the ray-conversion layer.

11. The method as claimed in claim 10, further comprising:

after forming the photodiode, forming a second metal layer over the photodiode, and then, simultaneously forming a signal line and a light-shielding layer covering the amorphous-silicon thin-film transistor by a single patterning process.

12. The method as claimed in claim 11, further comprising:

after forming the light-shielding layer, coating a resin material or depositing a transparent passivation film layer to form a passivation layer.

* * * * *